(12) United States Patent
Izatt et al.

(10) Patent No.: US 6,858,114 B2
(45) Date of Patent: Feb. 22, 2005

(54) LASER HYDROLYSIS OF POLYPEPTIDES

(75) Inventors: Jerald R. Izatt, Northport, AL (US); Alvin L. Winters, Tuscaloosa, AL (US); Mary P. Ouzts, Sewanee, TN (US)

(73) Assignee: The University of Alabama, Tuscaloosa, AL (US)

( * ) Notice: Subject to any disclaimer, the term of this patent is extended or adjusted under 35 U.S.C. 154(b) by 88 days.

(21) Appl. No.: 09/897,060

(22) Filed: Jul. 3, 2001

(65) Prior Publication Data

US 2003/0010620 A1 Jan. 16, 2003

(51) Int. Cl.$^7$ .......................... C07C 1/00; A61K 38/00
(52) U.S. Cl. ............... 204/157.61; 204/155; 204/157.6; 204/157.15; 530/332; 514/2
(58) Field of Search .......................... 204/157.61, 155, 204/157.6, 157.15, 157.64, 157.65, 157.68, 157.72, 157.87; 530/300, 332; 514/2

(56) References Cited

U.S. PATENT DOCUMENTS

| | | |
|---|---|---|
| 3,941,670 A | 3/1976 | Pratt, Jr. |
| 4,672,969 A | 6/1987 | Dew |
| 4,713,335 A | 12/1987 | Keyes |
| 4,714,676 A | 12/1987 | Keyes |
| 4,714,677 A | 12/1987 | Keyes |
| 4,716,116 A | 12/1987 | Keyes |
| 4,854,320 A | 8/1989 | Dew et al. |
| 4,880,512 A | 11/1989 | Cornelius et al. |
| 5,002,051 A | 3/1991 | Dew et al. |
| 5,145,863 A | 9/1992 | Dougherty et al. |
| 5,215,715 A | 6/1993 | Haswell et al. |
| 5,346,789 A | 9/1994 | Lewis et al. |
| 5,395,490 A | 3/1995 | Hoff et al. |
| 5,470,690 A | 11/1995 | Lewis et al. |
| 5,504,772 A | 4/1996 | Deacon et al. |
| 5,518,858 A | 5/1996 | Dyukova et al. |
| 5,573,831 A | 11/1996 | Suzuki et al. |
| 5,616,447 A | 4/1997 | Arioka |
| 5,772,855 A | 6/1998 | Johnson et al. |
| 5,776,575 A | 7/1998 | Hiraoka et al. |
| 5,791,352 A | 8/1998 | Reich et al. |
| 5,849,882 A | 12/1998 | Ping-Fan |
| 5,858,179 A | 1/1999 | Loda |
| 5,874,701 A | 2/1999 | Watanabe et al. |
| 5,883,349 A | 3/1999 | Kingston |
| 5,929,044 A | 7/1999 | Poppas |
| 5,972,457 A | 10/1999 | Matsuishi et al. |
| 6,071,956 A | 6/2000 | Slepian et al. |
| 6,090,911 A | 7/2000 | Petka et al. |
| 6,096,172 A | 8/2000 | Foley et al. |

FOREIGN PATENT DOCUMENTS

WO    WO 00/31544    6/2000

OTHER PUBLICATIONS

Michael Fountoulakis et al., "Hydrolysis and Amino Acid Composition Analysis of Proteins", Journal of Chromatography A, 826 (1998), pp. 109–134.

Kristin M. Kirsch et al., "Ultrastructure of Collagen Thermally denatured by Microsecond domain Pulsed Carbon Dioxide Laser", Arch Dermatol, vol. 132, Oct. 1998.

David L. Sanders et al., "Wound Healing and Collagen Thermal Damage in 7.5µsec Pulsed $CO_2$ Laser Skin Incisions", Lasers in surgery and Medicine 26:22–32 (20000.

Gholam a. Peyman et al., "Diagnostic and Surgical Techniques", Survey of Ophthalmology, vol. 28, No. 5., Mar.–Apr. 1984.

Andrés criado et al., "Fast Urinary Screening for Paracetamol using On–Line Microwave Assisted Hydrolysis and Spectrophotometric Detection", This Journal is © The Royal Society of Chemistry 2000, 125, pp. 1179–1183.

"Journal of Chromatography Biomedical Applications", vol. 491, No. 2, Jul. 21, 1989 (Biomedical applications, vol. 83, No. 2) This Issue Completes vol. 491.

Gary Englehart, "Microwave Hydrolysis of Peptides and Proteins for Amino Acid analysis", American biotechnology Laboratory, vol. 8, No. 15, Nov. 1990, pp. 30–34.

Andrej Shevchenko et al., "MALDI Quadrupole Time–of–Flight Mass Spectrometry: A Powerful Tool for Proteomic Research", Anal. Chem. 2000, 72, pp. 3132–2141.

Ian Davidson, "Hydrolysis of Samples for Amino Acid Analysis", Methods in Molecular Biology, vol. 64: Protein Sequencing Protocols.

N.V. Ozolina et al., "The Effect of Low–Intensity Laser Irradiation on the Hydrolytic Activity of Vacular Membrane Proton Pumps", Membr. Cell Biol. 1997, vol. 11 (1), pp. 157–159.

Christopher T. Rooke et al., "$CO_2$ Laser Welding Versus Conventional Microsuture Repair in Patch–Graft Urethroplasty", Urology, Jun. 1993, vol. 41, No. 6, pp. 585–589.

Katherina S. Kuhn et al., Determination of Glutamine in Muscle Protein Facilitates Accurate Assessment of Proteolysis and De Novo Synthesis–Derived Endogenous Glutamine Production $^{1-3}$, AM. J. Clinical Nutrition, 1999, 70;484–9.

*Primary Examiner*—Christopher R. Tate
*Assistant Examiner*—B. Dell Chism
(74) *Attorney, Agent, or Firm*—Oblon, Spivak, McClelland, Maier & Neustadt, P.C.

(57) ABSTRACT

The present invention relates to methods of hydrolyzing a protein (or peptide) by treating a protein (or peptide)-containing sample with a laser and associated apparatus for effectuating the hydrolysis.

29 Claims, 9 Drawing Sheets

Figure 5

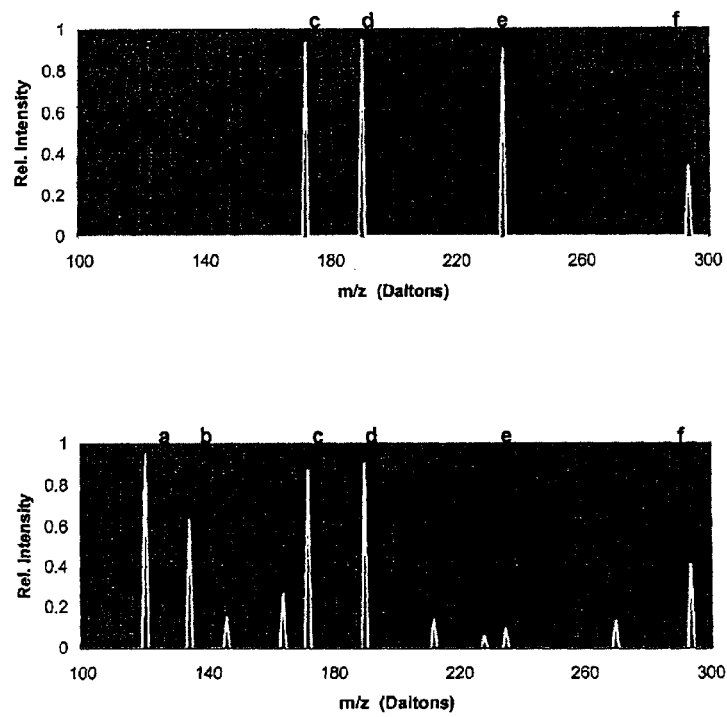

Figure 5. MALDI-TOF spectra of the Thr-Asp sample corresponding to the hydrolysis peak in figure 4, which was produced by 9P12 (~1054 cm$^{-1}$). Upper spectrum - before hydrolysis. Lower spectrum - after laser enhanced hydrolysis. Line e in each spectrum is located at an m/z ratio of 234.2, which corresponds to the dipeptide Thr-Asp. Lines a and b correspond to L-threonine (m/z =119.1) and L-aspartic acid (m/z =133.1), respectively. Lines c, d and f, which remain essentially constant in both spectra, result from the matrix used for the MALDI target. (Note that these are (M+H)$^+$ spectra and consequently the m/z values are one mass unit higher than the expected values.)

LASER HYDROLYSIS OF POLYPEPTIDES

BACKGROUND OF THE INVENTION

Field of the Invention

The present invention relates to methods of hydrolyzing a protein (or peptide) by treating a protein (or peptide)-containing sample with a laser and associated apparatus for effectuating the hydrolysis.

Discussion of the Background

Full protein hydrolysis followed by amino acid analysis and partial hydrolysis followed by peptide analysis are procedures basic to the characterization of a protein. As currently practiced, full hydrolysis of proteins typically requires heating the sample to 110° C. for up to 24 hours in a 6.0N hydrochloric acid solution (Hill, Robert L., in *Advances in Protein Chemistry*, Vol. 20, edited by C. B. Anfinson, Jr., M. L. Anson, J. T. Edsall, and F. M. Richards, (Academic Press, New York, 1965), pp. 37–107. Ozols, R., in *Methods in Enzymology*, Vol 182, edited by M. P. Deutscher, (Academic Press, New York, 1990), pp. 587–601.). These severe conditions sometimes degrade the amino acids that are produced. For example, degradation of hydroxyproline by oven hydrolysis interferes with its use for the analysis of connective tissue disorders (Brown, S., M. Worsford, and C. Sharp, Bio Techniques 30(1), 38–42, (2001)). Microwave heating of the sample can reduce the time to approximately 15 minutes (Dagani, Ron, Chemical and Engineering News 75(6), 26–33 (1997)), but the still higher and unevenly distributed temperatures produced by this procedure can likewise, and sometimes even more seriously, degrade some of the amino acid products (Pickering, Michael V. and Paul Newton, LGCC 8(10), 779–781 (1990)). Although some work has been done to assess preferential cleavage at particular peptide bond sites in conventional and microwave hydrolysis(Gobom, J., E. Mirgorodskaya, E. Nordhoff, et al, Anal. Chem. 72, 919–927 (1999)), neither of these techniques currently provides useful bond site selectivity. Hydrolysis at specific peptide bonds can be accomplished by digestion with trypsin or other proteases. This process provides a useful, but limited selection of bonds for cleavage. However, protease digestion also requires 6–24 hours in typical circumstances (Ausubel, F. M., *Current Protocols in Molecular Biology*, edited by F. M. Ausubel et al, (John Wiley and Sons, Inc., New York, 1994)). The slowness of conventional hydrolysis also entails long periods of exposure of the hydrolysis products to a boiling acid environment, often resulting in sample deterioration.

Accordingly, there is a need for more efficient and faster hydrolysis methods. The present inventors have discovered that the aforementioned problems, which exist in the hydrolysis of polypeptides and proteins, can be addressed by the present methods and apparatuses described herein. Laser enhanced hydrolysis avoids this problem by greatly reducing the exposure time. In some cases the HCl concentration can also be reduced, or eliminated entirely.

SUMMARY OF THE INVENTION

Accordingly, the principal objects of the present invention are: 1) to reduce the time required to hydrolyze polypeptides and proteins, 2) to permit continuous extraction of hydrolyzed material as the hydrolysis proceeds, 3) to reduce degradation of hydrolyzed material due to long exposure to the harsh process environment, 4) to provide specific bond-site selectivity by laser wavelength control, 5) to provide in situ hydrolysis capability by means of laser steering, 6) to provide multi-batch processing by splitting the laser beam between multiple sample irradiation sites.

Accordingly, one object of the present invention is a method of hydrolyzing of polypeptides comprising exposing the polypeptide to a tuneable molecular gas laser.

In one embodiment of the invention the polypeptide is collected after it is exposed to the laser.

In another embodiment of the invention the polypeptide is analyzed after it is collected.

In another embodiment of the invention the hydrolyzed proteins are separated and analyzed by mass spectroscopy.

In another embodiment of the invention polypeptide is in a solution or is immobilized on a solid support.

In another embodiment of the invention the hydrolyzed proteins are separated prior to being analyzed., for example by High Performace Liquid Chromatography (HPLC), ion exchange chromatography, liquid chromatography, gas chromatography, capillary electrophoresis, two dimensional combined chromatography-electrophoresis, 2D-gel electrophoresis.

In another embodiment of the invention the hydrolyzed amino acid sequence of the hydrolyzed polypeptide is determined.

In another embodiment of the invention the concentration of the polypeptide is determined after the polypeptide is hydrolyzed.

In another embodiment of the invention the concentration, identification or other analyses of the hydrolyzed polypeptide comprises MALDI-MS, ESI-MS and/or combinations of the two.

Another object of the present invention to facilitate the object method is an apparatus composed of a sample holder, a laser source, a sample collector, and a sample analyzer, wherein the laser source is positioned to direct the laser into a sample contained in the sample holder, the sample collector is positioned to collect sample from the sample holder; and wherein said sample analyzer is connected to the sample collector.

In another embodiment of the invention the apparatus is coupled to one or more computer or electronic devices to effectuate analysis of the data obtained from the sample analyzer.

In another embodiment of the invention the apparatus is composed of a means for holding a sample, a means to provide a tuneable molecular gas laser, a means to collect the sample, and a means to analyze the sample analyzer, wherein said laser is positioned to direct the laser into said sample holding means, wherein the sample collecting means is positioned to collect sample from the sample holding means; and wherein said sample analyzing means is connected to the sample collecting means.

The above objects highlight certain aspects of the invention. Additional objects, aspects and embodiments of the invention are found in the following detailed description of the invention.

Triangles denote % hydrolysis. Squares indicate positions of successive laser lines from 9P30 on the left side to 9P8 on the right. % hydrolysis was measured by reverse phase high performance liquid chromatography (RP-HPLC)

Figure 4:
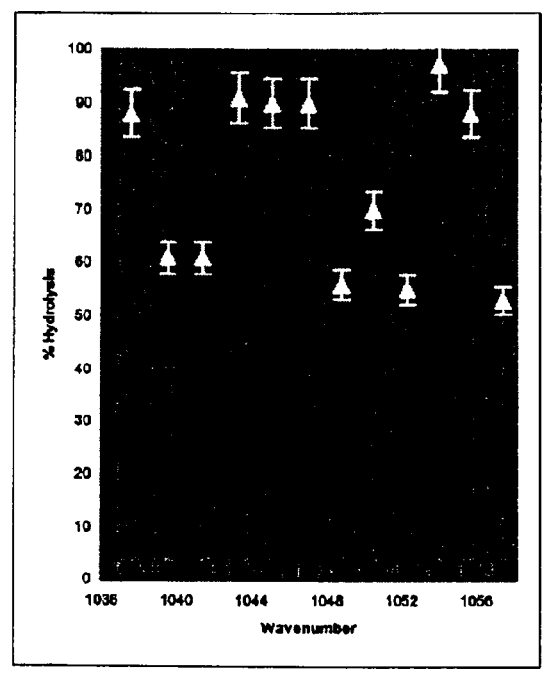

FIG. 4: Spectral dependence of laser enhanced hydrolysis for 25 mM Thr-Asp in 6N HCl. Laser operated 1.25W. Triangles denote % hydrolysis. Squares indicate positions of successive laser lines from 9P30 on the left to 9P8 on the right. % hydrolysis was measured by (RP-HPLC).

FIG. 5: MALDI-TOF spectra of the Thr-Asp sample corresponding to the hydrolysis peak in FIG. 4, which was produced by 9P12 (~1054 cm$^{-1}$). Upper spectrum-before hydrolysis. Lower spectrum-after laser enhanced hydrolysis. Line e in each spectrum is located at an m/z ratio f234.2, which corresponds to the dipeptide Thr-Asp. Lines a and b correspond to L-threonine (m/z=119.1) and L-aspartic acid (m/z=133.1), respectively. Lines c, d and f, which remain essentially constant in both spectra, result from the matrix used for the MALDI target. (Note that these are (M+H)$^+$ spectra and consequently the m/z values are one mass unit higher than the expected values).

Figure 6:
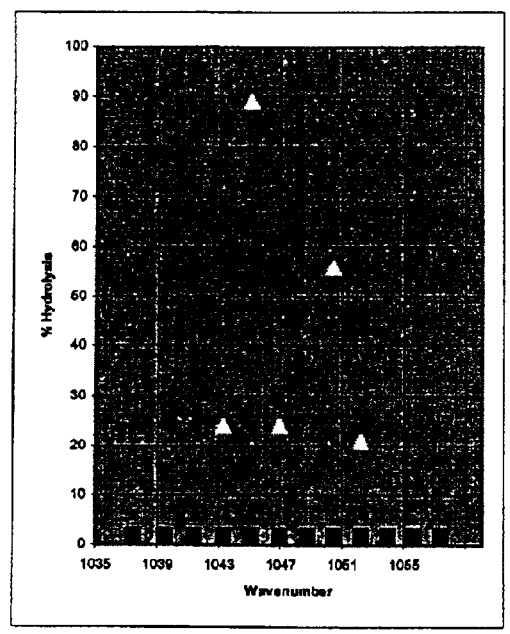

FIG. 6: Spectral dependence of laser enhanced hydrolysis spectrum for BSA. Laser operated at 1.0W. Triangles denote % hydrolysis. Squares indicated positions of successive laser lines from 9P30 on the left to 9P8 on the right. % hydrolysis was measured using ninhydrin calorimetric assay.

Figure 7:
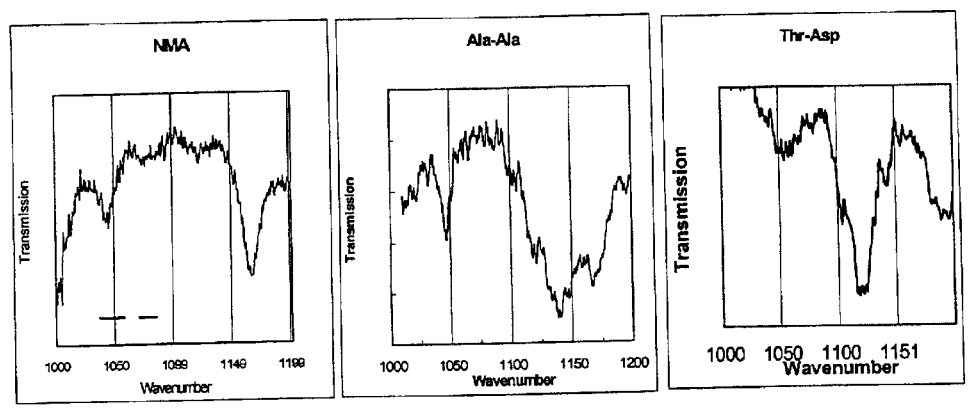

FIG. 7: Spectra of NMA, Ala-Ala and Thr-Asp in $H_2O$ solution. Note the persistence of the weak absorption peak near 1050 cm$^{-1}$. The horizontal lines in the NMA spectrum show the position of the 9P laser branch near 1050 cm$^{-1}$ and also the 9R branch at higher wavenumbers.

Figure 8:
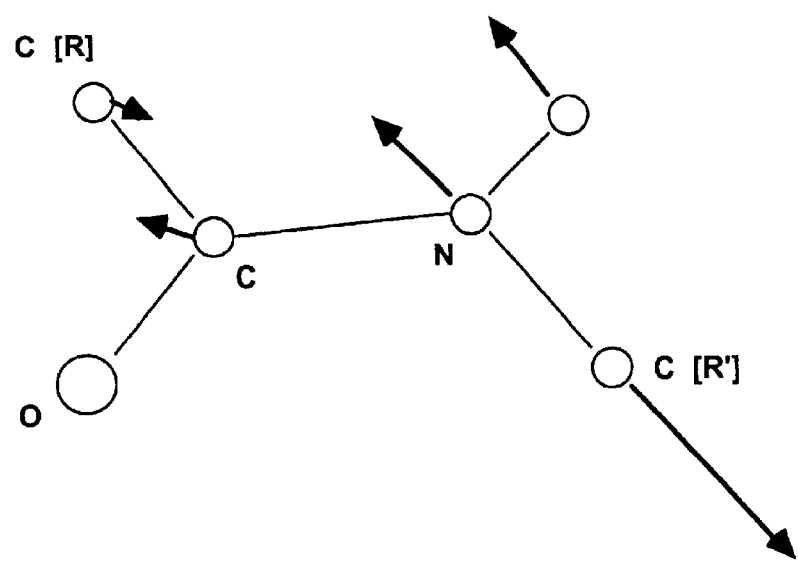

FIG. 8: NMA normal vibrational mode at 1044 cm$^{-1}$. In NMA both R and R' are $CH_3$ groups. In a dipeptide they are the amino acids joined by the peptide bond.

Figure 9:
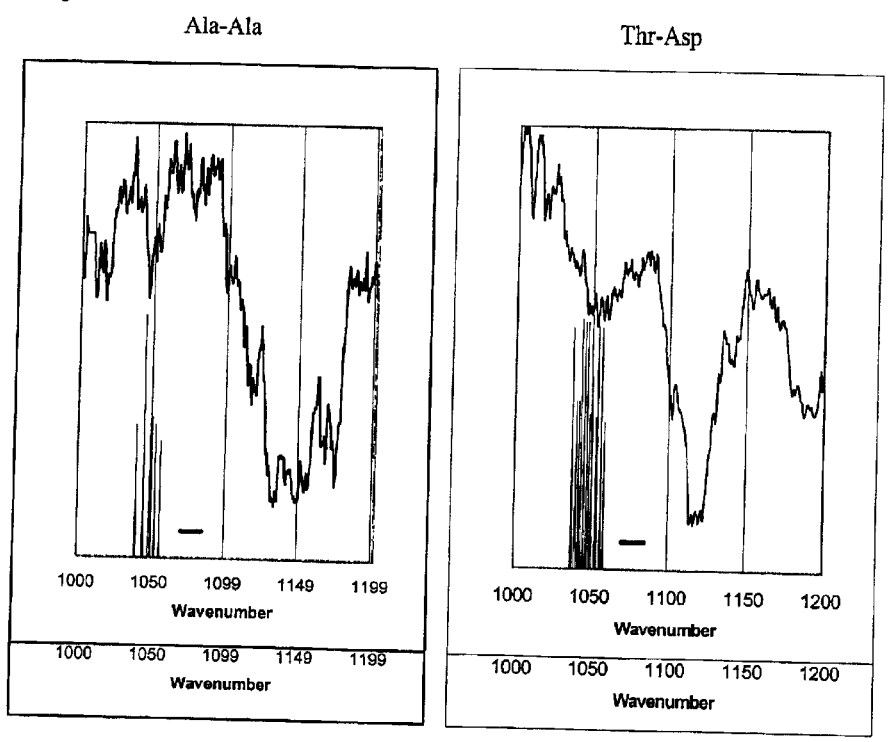

FIG. 9: 9P laser lines used to irradiate the sample are indicated by the vertical lines near 1050 cm$^{-1}$. The height of each line is proportional to the extent of hydrolysis observed. The tallest represent 100% hydrolysis. The short horizontal bar near 1075 cm$^{-1}$ shows the position of the 9R branch of the laser output. A segment of each transmission spectrum is also shown.

DETAILED DESCRIPTION OF THE INVENTION

Unless otherwise defined, all technical and scientific terms used herein have the same meaning as commonly understood by one of ordinary skill in the arts of molecular biology and laser optics. Although methods and materials similar or equivalent to those described herein can be used in the practice or testing of the present invention, suitable methods and materials are described herein. All publications, patent applications, patents, and other references mentioned herein are incorporated by reference in their entirety. The materials, methods, and examples are illustrative only and are not intended to be limiting.

Reference is made to standard textbooks of molecular biology and optics that contain definitions and methods and means for carrying out basic techniques, encompassed by the present invention. See, for example, Maniatis, T., E. Fritsch, and J. Sambrook, Molecular Cloning: A Laboratory Manual, Cold Spring Harbor Laboratory, New York (1982), Sambrook, J., E. F. Fritsch, and T. Maniatis, Molecular Cloning: A Laboratory Manual, 2nd edition, Cold Spring Harbor Laboratory, New York (1989), Sambrook, J. and D. W. Russell, Molecular Cloning, A Laboratory Manual, 3rd edition, Cold Spring Harbor Laboratory, New York (2001), Ausubel, F. A., R. Brent, R. E. Kingston, D. D. Moore, J. G. Seidman, J. A. Smith, and K. Struhl (eds.) Current Protocols in Molecular Biology, (John Wiley & Sons, New York (2001)), Coligan, J. E., B. M. Dunn, H. L. Ploegh, D. W. Speicher, and P. T. Wingfield (eds.), Current Protocols in Protein Chemistry, (John Wiley & Sons, New York (2001)), Pedrotti, F. L. and Pedrotti, L. S., Introduction to Optics, 2nd edition, (Prentice Hall, New Jersey (1993)), or other, and the various references cited therein.

The present inventors have developed a procedure which accomplishes hydrolysis on a time scale of seconds, permits continuous extraction of hydrolyzed product, and provides a significant increase in bond selectivity. The protein (or peptide) sample is prepared according to a standard acid hydrolysis protocol and then irradiated with a low power, continuous wave (cw) $CO_2$ laser rather than being heated in a conventional or microwave oven. The liquid sample evaporates slowly and smoothly due to laser heating at the surface of the liquid. This process produces no boiling or other visible turbulence. The bulk of the sample remains at a temperature below 60° C. Vapor evolved from the surface rises through a containment column above the liquid surface and is continuously irradiated by the laser as it does so. The vapor is then condensed and collected, and the condensate contains the hydrolyzed material. Condensate begins to accumulate within a few seconds after the sample is exposed to the laser beam, and it can be removed from the apparatus continuously. The enhancement of hydrolysis by the laser results from a non-thermal process that occurs in the vapor phase. This is evidenced by the fact that the extent of hydrolysis is strongly dependent on the wavelength to which the laser is tuned. The wavelength(s) required for maximal hydrolysis change(s) from one dipeptide segment to another.

It appears that the laser catalyzes acid hydrolysis of polypeptides by exciting a fundamental vibrational mode associated with the peptide bond structure. However, the wavelength sensitivity of laser enhanced hydrolysis is much sharper than the corresponding vibrational feature that we have tentatively identified in the spectra of liquid samples, and this suggests the existence of spectral fine structure that can only be observed in the vapor state.

Protein hydrolysis has broad applicability in many areas relating to medical research and practice, including pharmacology, and toxicology. It is also important in food processing, pollution monitoring, and many other applications of biochemistry and biophysics, including the new and rapidly growing field of proteomics. In addition to its use for the analysis of protein structure, polypeptide hydrolysis can also be used in the production of amino acids. The following examples illustrate the potential advantages of applying laser enhanced hydrolysis to some of these disciplines.

PROTEOMICS The genomes of a relatively large number of organisms, including the human, have been sequenced. The global protein expression of a genome has been named the proteome (Wasinger, V. C., S. J. Cordwell, A. Cerpa-Poljak, et al, Electrophoresis 16, 1090–1094 (1995)). Elucidating the expression of the genome in terms of the proteins whose synthesis it encodes, as individual genes act either singly or in concert, is an enormous undertaking. It has fostered the new discipline of proteomics (Rabilloud, T., and I. Humphrey-Smith, in *Proteome Research: Two-Dimensional Gel Electrophoresis and Identification Methods*, edited by T. Rabilloud, (Springer Verlag, Berlin, 2000), pp. 1–8). An important procedure in proteomic analysis is the automated processing and identification of proteins separated in large two-dimensional arrays in polyacrylamide gels (2D-gels). Traditionally, identification of separated proteins was accomplished either by reaction with specific antibodies or by determining the amino acid sequence. The former technique is used to make singular identifications and is highly dependent on the ability to obtain antibodies with the appropriate specificity. In its traditional form the latter technique is very time-consuming. Many proteins are blocked for analysis at the amino terminal end and the amount of protein available for sequencing is limited. The relatively new technique of matrix assisted desorption and ionization-mass spectroscopy (MALDI-MS) avoids these general problems. MALDI-MS identifies proteins by precise measurement of the characteristic fragments created by trypsin digestion of the protein. The masses are then compared to large data banks of fragment sequences from both known and unknown proteins In current 2D-gel/MALDI-MS practice samples are excised from individual protein spots in the array and each protein is digested with trypsin in a separate batch hydrolysis. Trypsin digestion, which requires at least 6–8 h, is the rate-limiting step. The other sequential steps in the process are highly automated and occur on a time scale of minutes. Laser enhanced hydrolysis has the potential to overcome the digestion time bottleneck. In principle, laser enhanced hydrolysis of the protein spots could also be accomplished in situ by using a scanning mechanism to irradiate the 2D-gel spots sequentially and very rapidly. In this procedure it would be necessary to collect the hydrolyzed material from each spot and correlate each such sample with its position in the original 2D-gel. Subsequent mass spectrometer analysis could then be performed. Alternatively, a hollow, steerable light guide could be used to direct the laser beam onto each protein spot on a polyacrylamide 2D-gel and simultaneously collect the vaporized/hydrolyzed material produced by the laser. The latter could then be mixed with the appropriate chemicals to produce an appropriate matrix for mass spectrometer use, and the latter deposited on a spectrometer sample plate in a sequence directly correlated with the spot distribution on the original 2D-gel.

Recent advances in mass spectrometry have been coupled with innovative computational tools and massive databases to accelerate the growth of proteomic research using 2D-gels. Typically, after trypsin digestion of a protein sample taken from one of the array sites, the mass spectrometer measures the masses of the resulting peptides, and these masses are compared to predicted peptide masses stored in continually growing data bases. Sometimes a single peptide pattern suffices for the identification of a protein However, finding the masses of a few of its peptide fragments by this process does not always provide unambiguous identification, and the peptides are sometimes further fragmented and analyzed in a second mass spectrometer to analyze the peptide patterns (Fields, S., Science, Vol. 291, 1221–1224, (16 Feb. 2001)). A supplemental technique for bond-site-selective hydrolysis of large proteins into smaller peptides would speed the characterization of a protein by simplifying the spot identification in 2D-gels using mass spectrometry (Gobom, J., E. Mirgorodskaya, E. Nordhoff, et al, Anal. Chem. 72, 919–927 (1999) and Soga, T., Anal. Chem. 72, 1236–1241 (2000)).

Laser hydrolysis of different peptide bond sites is strongly dependent on the wavelength at which the laser is operated. In some cases controlled peptide bond breaking can be achieved by wavelength selection, thus increasing the collection of fragmentation sites currently provided by pepsin and other proteases. Moreover, if required, laser enhanced hydrolysis could be used to rapidly separate the resulting peptides into their constituent amino acids. Note that comparable advantages could also be realized by using laser enhanced hydrolysis together with other analytical techniques that are important in proteomics, including high performance liquid chromatography (HPLC) and nuclear magnetic resonance (Gobom, J., E. Mirgorodskaya, E. Nordhoff, et al, Anal. Chem. 72, 919–927 (1999) and Soga, T., Anal. Chem. 72, 1236–1241 (2000)).

FOOD PROCESSING Protein functionality plays an important role in the food industry, including both academic and commercial activities. The amino acid content of food and food supplements is analyzed to ensure the basic food quality of proteins and peptides in the food mix. The measure of food quality is presently quantified in the protein digestibility-corrected amino acid score (PDCAAS) (FAO/WHO Nutrition Meetings, Report Series 51; Food and Agriculture Organization/World Health Organization: Rome, 1991). Although this particular classification scheme is subject to further refinement, amino acid analysis is and will continue to be an important element in the assessment of food quality (Schaafsma G., J. Nutr. 130, 1865–1867S (2000).

One of the principal problems with prior hydrolysis methods in food analysis is once again the time required for batch acid hydrolysis. Once the peptide bonds of a protein are broken, the resulting amino acids are identified by standard analytical procedures that require much less time than the hydrolysis itself, e.g., ion exchange chromatography, HPLC, capillary electrophoresis, and mass spectroscopy. Since laser enhanced hydrolysis produces hydrolyzed proteins immediately and continuously, our invention has the potential for direct and continuous linkage of the hydrolysis and analytical processes within one instrument. In addition, since laser enhanced hydrolysis only requires laser powers of the order of one watt and $CO_2$ lasers producing 100 or more times that power are readily available, it would be possible to split the beam and irradiate many samples simultaneously.

Within the scope of the present invention any line tuneable molecular gas laser can be employed in the hydroysis of protein (or peptide) samples. As used herein "line tuneable molecular gas laser" is understood to mean Molecular gas lasers that produce infrared radiation, as required by this application, are generally excited by an electrical discharge. The discharge itself, sometimes in concert with one or more of a variety of intramolecular collision processes, can sometimes produce a population inversion between a set of excited rovibrational states of the molecules and their ground state. In other cases (for example the $CO_2$ laser), this processs can also produce a population inversion between between pairs of rotational levels where each belongs to to a different excited vibrational state. In either case, there is a large number of rotational levels with energy spacings small compared to that associated with the vibrational transition. By controlling the losses of the laser cavity in an appropriate way the laser can be made to oscillate on a single ro-vibrational transition whose energy, and hence frequency or wavelength, is determined by the particular rotational state that is excited in the upper state and the selection rules that specify the particular rotational level in the lower vibrational state to which a transition is allowed. The cavity losses can be controlled so that they are small enough to permit oscillation at only one given frequency; i.e., the one corresponding to the transition on which oscillation is wanted, by using a diffraction grating inside of the cavity or by one of the other means we have suggested. Since each such transition involves a fixed change in vibrational state plus a much less energetic change in rotational state, the frequency of oscillation changes in small steps as the diffraction grating or other device is used (tuned) to single out successive rotational states. Since the spacing of the rotational states is finite this process produces a succession of laser outputs (laser lines) with finite frequency separations. Using the diffraction grating, or other device, to scan the laser output across this comb of fixed frequencies is called line-to-line tuning.

Preferably such line tuneable molecular gas lasers are $N_2O$ or $CO_2$ gas lasers. Examples of the $N_2O$ lasers are continuous wave (cw) $^{14}N_2^{16}O$ type gas lasers. Examples of the $CO_2$ gas types which can be employed in the laser are the cw or pulsed type lasers of $^{12}C^{16}O_2$ gas, $^{12}C^{16}O^{18}O$ gas, $^{12}C^{18}O_2$ gas, $^{13}C^{16}O_2$ gas, $^{13}C^{18}O_2$ gas, $^{14}C^{16}O_2$ gas, $^{14}C^{18}O_2$ gas, $^{12}C^{17}O_2$ gas, and $^{13}C^{16}O^{18}O$ gas. The laser may also be a mixture of two or more of these gases (Freed, C., "$CO_2$ Isotope Lasers and Their Applications in Tunable Laser Spectroscopy", in *Tunable Lasers Handbook*, Duarte, F. J., Ed., pp. 9–31, (Academic Press, New York, 1995)).

Such line tunable lasers can be tuned in accordance with the standard protocols in the art (Mollenauer, L. F., White, J. C., Pollock, C. R., Eds., *Tunable Lasers*, (Springer-Verlag, Berlin, 1992); Duarte, F. J., Ed., *Tunable Lasers Handbook*, (Acedemic Press, New York, 1995)). For example, the laser can be tuned over the entire set of lines on which it can oscillate with an intracavity diffraction grating or assembly of gratings (Sze, R. C. and Harris, D. G., "Tunable Excimer Lasers", in *Tunable Lasers Handbook*, Duarte, F. J., Ed., pp. 33–61, (Academic Press, New York, 1995), Izatt, J. R., Rob, M. A., Zhu, W.-S., Two- and Three-Grating Resonators for High-Power Pulsed CO2 Lasers". Appl. Optics 30, 4319 (1996)), or with an intracavity prism or set of prisms (Duarte, F. J., "Narrow-Linewidth Laser Oscillators and Intracavity Dispersion", in *Tunable Lasers Handbook*, Duarte, F. J., Ed., pp. 9–31, (Acedemic Press, New York, 1995)). A laser of this type can also be stabilized to oscillate at the center of a specific line within its overall oscillation range by using an intracavity Fabry-Perot etalon or various other intracavity interference devices (Jaeger, T., and Wang, G., "Tunable High-Pressure Infrared Lasers", in *Tunable Lasers*, Mollenauer, L. F., White, J. C., Pollock, C. R., Eds., pp. 303–328 (Springer-Verlag, Berlin, 1992)), or with various selective absorption schemes (Izatt, J. R. and Mathieu, P., "Far-infrared Lasers Pumped with Tunable Narrow Band $CO_2$-TEA Lasers", Can. J. Phys. 58, 1403–1415 (1980)). Some of these techniques have been used primarily with pulsed lasers but can be readily adapted for use with cw lasers as well.

The $CO_2$ laser can be tuned to operate on many different lines in the 0001–0200 band, centered at 9.4 µm, or in the 0001–1000 band, centered at 10.4 µm. Each of these ro-vibrational bands has an R branch with $\Delta J=+1$ and a P branch with $\Delta J=-1$. For simplicity, a given laser line can be designated by 9 or 10 to indicate the ro-vibrational band, by P or R for the branch, and finally by the J-number of the initial state. Prefered ranges of line tuning include from about 9R2 to about 9R60, from about 9P2 to about 9P60, from about 10R2 to about 10R60, and/or about 10P2 to about 10P60. For example, 9P22 is a $\Delta J=-1$ line in the 9.4 µm band that originates from the J=22 level. The $^{12}C^{16}O_2$ laser lines for which results will be given here are tabulated below.

| Laser Line | Wavenumber (cm-1) | Wavelength (µm) |
|---|---|---|
| 9P30 | 1037.43 | 9.639 |
| 9P28 | 1039.37 | 9.621 |
| 9P26 | 1041.28 | 9.604 |
| 9P24 | 1043.16 | 9.586 |
| 9P22 | 1045.02 | 9.569 |
| 9P20 | 1046.85 | 9.552 |
| 9P18 | 1048.66 | 9.536 |
| 9P16 | 1050.44 | 9.520 |
| 9P14 | 1052.20 | 9.504 |
| 9P12 | 1053.02 | 9.488 |
| 9P10 | 1055.63 | 9.473 |
| 9P8 | 1057.30 | 9.458 |

Within the context of the present invention "isolated" or "purified" means separated out of its natural environment.

Within the context of the present invention "Polypeptides", "proteins" or "peptides" are understood as meaning peptides or proteins which comprise two or more amino acids bonded via peptide bonds.

Prior to exposing a protein sample to the laser, the proteins can be left in their native state, modified by chemical treatment, e.g., alkylated, methylated, phosphorylated, etc., partially purified, and purified depending on the desired product. The concentration of peptide or protein in the sample can be determined spectrophotometrically, spectrofluorometrically, and by colorimetric assays, such as biruet, Hardee-Lowry, bicinchinoic acid, nihydrin reaction, and Bradford (dye-binding) assay, and conventional acid hydrolysis followed by amino acid analysis (Simonian, M. H., In Current Protocols in Protein Science, edited by J. E. Coligan, B. M. Dunn, H. L. Ploegh, et al. (John Wiley and Sons, Inc., New York (2001), Lovrien, R., and D. Matulis, In Current Protocols in Protein Science, edited by J. E. Coligan, B. M. Dunn, H. L. Ploegh, et al. (John Wiley and Sons, Inc., New York (2001)).

Proteins may be partially purified by (1) cell fractionation, e.g., differentiation centrifugation, gel filtration, electrophoresis, immunoadsorption, lectin adsorption, density shift using digitonin or colloidal gold conjugate, and carbonate extraction (Castle, J. D., In Current Protocols in Protein Science, edited by J. E. Coligan, B. M. Dunn, H. L. Ploegh, et al. (John Wiley and Sons, Inc., New York (2001)), (2) selective precipitation, e.g., salting out, isoionic precipitation, organic cosolvent, protein exclusion, polyelectrolytes, metallic and polyphenolic heteropolymer anions, hydrophobic ion pairing, ligands, ligand coprecipitation, and metal ions (Lovrein, R. E., and D. Matulis, In Current Protocols in Protein Science, edited by J. E. Coligan, B. M. Dunn, H. L. Ploegh, et al. (John Wiley and Sons, Inc., New York (2001)), (3) sequential solubilization (Molloy, M. P., B. R. Herbert, B. J. Walsh, et al., Electrophoresis 19, 837–844 (1998)), (4) differential extraction based on the partition coefficient (Shibusawa, Y., In Separation of protein by high-speed countercurrent chromatography, edited by Y. Ito and W. D. Conway (John Wiley and Sons, Inc. (1996)), (5) specific adsorption to protein recognition molecules (PRMs) in microarrays (Jenkins, R. E., and S. R. Penington, Proteomics 1, 13–29 (2001)). (6) conventional chromatography, e.g., ion-exchange, gel filtration, hydrophobic interaction, chromatofocusing, hydroxylapatite, and various HPLC systems. (Williams, A., In Current Protocols in Protein Science, edited by J. E. Coligan, B. M. Dunn, H. L. Ploegh, et al. (John Wiley and Sons, Inc., New York (2001), Williams, A.

and V. Frasca, In Current Protocols in Protein Science, edited by J. E. Coligan, B. M. Dunn, H. L. Ploegh, et al. (John Wiley and Sons, Inc., New York (2001)), and conventional electrophoresis in 1D-(Gallagher, S. R., In Current Protocols in Protein Science, edited by J. E. Coligan, B. M. Dunn, H. L. Ploegh, et al. (John Wiley and Sons, Inc., New York (2001)). and 2D polyacrylamide gels (O'Farrel, P. H., J. Biol. Chem. 250, 4007–4021 (1975), Harper, S., J. Mozdzanowki, and D. Speicher, In Current Protocols in Protein Science, edited by J. E. Coligan, B. M. Dunn, H. L. Ploegh, et al. (John Wiley and Sons, Inc., New York (2001)).

The purified or partially purified protein sample can then be subjected to the laser until all of the aqueous phase of the sample has been vaporized. The time of exposure is dependent on the level of laser energy and sample volume, i.e., the rate of vaporization is porportional to the level of laser energy. The hydrogen ion content of the aqueous phase can be supplied with inorganic and organic acids. The aqueous phase can be fluid, in a gel matrix, such as polyacrylamide gels, or other types of polymer based gels. The acids can be placed directly in the protein solution or introduced by diffusion of the acid vapor. The irradiation of the protein sample can occur in three ways, depending on the products desired. (1) Sample holders for protein solutions can be constructed from any nonreactive, acid stable, and thermostable material, such as glass, polypropylene, teflon, stainless steel or other suitable plastics or metal alloys. The design of the sample holder requires a port for adding the protein solution, an infrared transparent window for transmission of the laser beam, a sample reservoir, a collection device (condenser or activated carbon) to capture the laser generated vapor, and a port to remove processed material for analysis and other uses. Additional ports can be added for the continuous addition of aqueous phase samples and continuous harvest of the laser generated vapor products. The sample well can be constructed with dimensions that will permit irradiation of the entire surface of the protein solution simultaneously, thus essentially all of the vapor has to pass through the laser beam before collection. (2) The protein solution can be embedded in a gel matrix. The hydrogen ion content of the sample can be controlled by direct addition of the acid or by diffusion of the acid vapor. The laser beam is directed to the surface of the gel matrix with the embedded protein. The collection apparatus can be constructed of any of the inert materials mentioned above. The apparatus should contain an open port for capturing the vaporized sample, an infrared transparent window for transmitting the laser beam, a collection device (condenser or activated carbon), a port for removing processed material for analysis, and a port to provide a negative pressure in the entire apparatus to ensure collection of the vapor from the gel surface. (3) The protein sample can be dried on a surface e.g., a fingerprint. The sample can then be exposed to water and acid vapor that will provide the appropriate chemical environment for laser hydrolysis. The laser beam can then be directed to the dried protein surface through a infrared transparent window, and the collection apparatus as described above would capture the products. In all three cases, the port for harvesting the hydrolyzed products can be used to monitor the rate of laser hydrolysis on a continuing basis.

Following laser treatment the hydrolyzed products (amino acids and peptides) can be analyzed by their separation into individual components using one or a combination of the protein purification techniques listed above. Isoelectric focusing coupled with SDS-PAGE and HPLC are common techniques for analysis. In addition, a variety of capillary electrophoresis techniques can be used (Veillon, J. F., C. Ramon, and N. Bihoreau, In Capillary Electrophoresis in Biotechnology and Environmental Analysis, edited by H. Parves, P. Caudy, S. Parves, and P. Roland-Gosselin (VSP BV, The Netherlands (1997), G. Lunn, Capillary Electrophoresis, Methods for Pharmaceutical Analysis (John Wiley and Sons, Inc., New York (1999)). These include cocapillary zone electrophoresis (CCZE) micellular electrokinetic capillary chromatography (MEKC), capillary isoelectric focusing (CIEF), capillary gel electrophoresis (CGE), and capillary isotachophoresis (CITP) (Oda, R. P., and J. P Landers, In Handbook of Capillary Electrophoresis, 2nd edition, edited by J. P. Landers (CRC Press, Boca Raton (1997)).

However, the standard procedure for amino acid and peptide analysis is RP-HPLC with precolumn derivitization using phenylisothiocyanate (PITC) to react with the free amino groups of amino acids to form phenylthiocarbamyl (PTC) amino acid derivatives. The separated amino acids are detected by UV adsorbance and identified by comparison of their retention times on C4, C8, or C18 columns with amino acid and peptide standards (Crabb, J. W., K. H. West, W. S. Dodson, and J. D. Hulmes, In Current Protocols in Protein Science, edited by J. E. Coligan, B. M. Dunn, H. L. Ploegh, et al. (John Wiley and Sons, Inc., New York (2001)). Other means of detecting the separated amino acids and peptides and their derivatives include UV absorbance, fluorescence, electrochemical, refractive index, evaporative light scattering, (Snyder, L. R., J. J. Kirkland, and J. L. Glajch. Practical HPLC Method Development, 2nd edition (John Wiley & Sons, Inc., New York (1997)), and mass spectrometry (Tomer, K. B., L. J. Deterding, and C. E. Parker, In Capillary Electrophoresis in Biotechnology and Environmental Analysis. edited by H. Parvez, P. Caudy, S. Parvez, and P. Roland-Gossellin (VSP BV, The Netherlands (1997)).

Derivatives of the amino acids and peptides may be made prior to or after the separation steps listed above to aid in the separation process or to increase the sensitivity of detecton (Lui, Y-M., and S. Zhao, LCGC 19, 414–420 (2002)). Derivatizing agents commonly used to form chromotags and fluorotags of amino acids and peptide are PITC, o-phthaldehyde (OPA), 4-dimethylaminiazobenzene-4-sulfonyl chloride (Dabsyl-Cl), fluorescamine, dimethylaminonaphthalene-1-sulfonyl chloride (Dansyl-Cl), 7 chloro-4-nitrobenzene-2-oxa-1,3-diazole (NBD-Cl), and 7 fluoro-4-nitrobenzene-2-oxa-1,3-diazole (NBD-Fl). These and other types of derivatizing agents may be employed within the context of the present invention.

Electrospray ionization mass spectrometry has also been used to identify amino acids following capillary electrophoresis (Soga, T., and D. N. Heiger, Anal. Chem. 72, 1236–1241 (2000)). However, the greatest potential for both electrospray ionization and matrix-assisted laser desorption ionization mass spectrometry (ESI-MS and MALDI-MS, respectively) is in the rapid identification of peptides (Cotter, R. J., Time-of-flight Mass Spectrometry Instrumentation and Application in Biological Research (American Chemical Society, Washington, D.C. (1997), Schürenberg, M., K. Driesewerd, and F. Hillenkamp, Anal. Chem. 71, 221–229 (1999)). The signals generated with these techniques can be compared to internet databases, such as NCBInr, Genpept, Swiss Prot, Owl, and dbEST using software programs, such as MS-Fit and MS-Tag (Jiménez, C. R., L. Huang, Y. Qui, and A. L. Burlingame, In Current Protocols in Protein Science, edited by J. E. Coligan, B. M. Dunn, H. L. Ploegh, et al. (John Wiley and Sons, Inc., New York (2001)). Additonal methods of mass spectrometry identification include using quadrupole ion trap mass spectrometry and software called SEQUEST for database matching (Moore, R. E., M. K. Young, and T. D. Lee, In Current Protocols in Protein Science, edited by J. E. Coligan, B. M. Dunn, H. L. Ploegh, et al. (John Wiley and Sons, Inc., New York (2001)).

EXAMPLES

Figure 1:
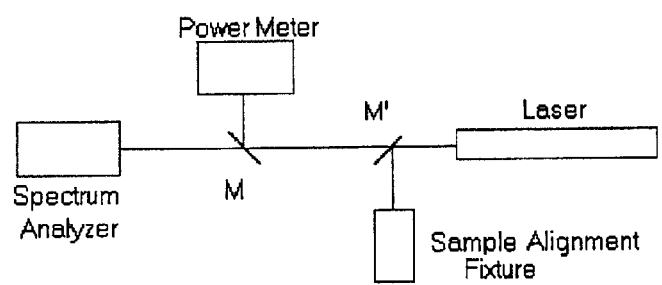
FIG. 1: Sample irradiation geometry
Figure 2:
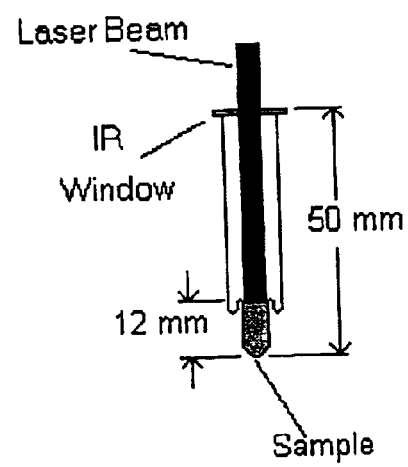
FIG. 2: Sample cell schematic

LASER HYDROLYSIS A schematic diagram of the demonstration setup is shown in FIG. 1. The glass sample cell is shown in FIG. 2. The cw $CO_2$ laser is operated in the $TEM_{00}$ mode at a power of about 1.0 watt and tuned by means of a diffraction grating to oscillate on one of the ro-vibrational lines in the conventional laser bands between 9 and 11 $\mu$m. The laser beam is steered onto the surface of the hydrolysis sample by a system of mirrors, represented schematically by M and M'. The collimated Gaussian beam incident on the sample has a beam width of ~1.0 mm. Alternatively, these mirrors can also be used to direct the beam to a power meter or a spectrum analyzer.

The sample solution is placed in the narrow lower section of the cell and has a volume between 40 and 80 $\mu$l. When the laser beam is directed onto the sample a thin layer near the surface of the liquid is rapidly heated and the sample begins to vaporize. (Note that at these wavelengths the penetration depth of the sample, which is largely composed of water, is ~20 $\mu$m. The penetration depth is the depth at which propagation through the absorbing sample reduces the beam intensity to 1/e times its intensity at the surface, where e is the base of natural logarithms and has a numerical value of approximately 2.72.) During this process there is no boiling or visible turbulence in the bulk of the sample. The vapor issuing from the surface mounts the enclosed column above the surface while being continuously irradiated by the laser. The vapor cools, condenses onto the cell wall, coalesces, runs down the wall, and is trapped in the lip. After 5–30 minutes of irradiation, depending on sample volume and laser power, all of the liquid has been transferred from the bottom of the cell to the lip by this process. Taking the maximum irradiation time to be 30 minutes for an 80 $\mu$l sample, processed material is thus produced continuously at a rate of at least 2.7 ml/min or 45 nl/sec. The processed sample is removed from the reflux lip with a micropipette. If the irradiation is terminated while there is still liquid in the bottom of the cell this liquid can likewise be sampled.

Figure 3:
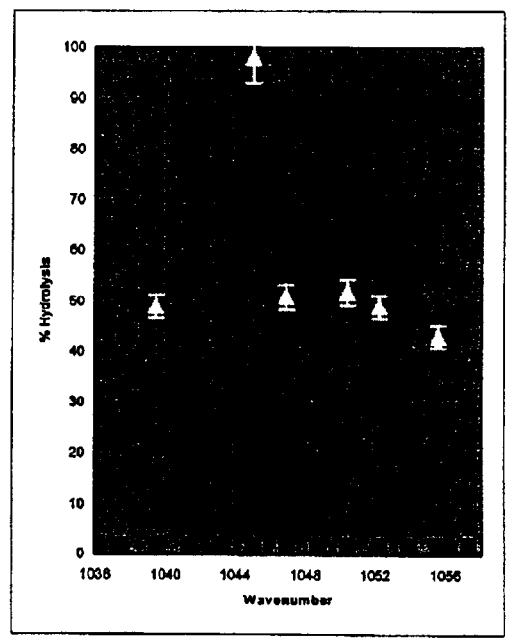
FIG. 3: Spectral dependence of laser enhanced hydrolysis for 25 mM Ala—Ala in 6N HCl. Laser operated at 1.25W.

When the laser is tuned to an appropriate laser line, sample extracted from the lip at any time during the irradiation process is strongly hydrolyzed. Sample from the bottom of the cell shows significantly less hydrolysis, independent of the laser line. The latter is consistent with laser heating of the whole sample and its container by the absorbed laser energy and by partial reflux of vapor before it escapes the well. The entire cell reaches an equilibrium temperature of ~60° C. When the laser is tuned to a line that does not enhance hydrolysis, sample taken from the lip at any time displays about the same level of hydrolysis as material extracted from the well. The laser wavelength required to produce enhanced hydrolysis in the sample collected from the lip varies from one dipeptide to another, depending on the R groups adjacent to the peptide bond that is to be broken. These findings are illustrated in FIGS. 3 and 4 where hydrolysis spectra for Thr-Asp and Ala-Ala are compared. FIG. 5 is an example of mass spectrographic results that illustrate the decrease in the parent dipeptide and the consequent growth of the corresponding amino acids brought about by laser enhanced hydrolysis.

The dipeptide samples used in this demonstration were dissolved in 6.0 N HCl, just as in the traditional procedure. However, they were subjected to laser irradiation, as has been described above, rather than being heated to 110° C. for 24 h. To provide a comparative control a sample of each dipeptide was also hydrolyzed by standard hydrolysis conditions (6.0 N HCl, 110° C., 24 h). For samples and controls three different methods were used to measure the extent of hydrolysis and to identify the hydrolysis products: 1) thin layer chromatography, 2) RP-HPLC, and 3) matrix assisted laser desorption ionization—time of flight mass spectroscopy (MALDI-TOF). All three methods provided unambiguous identification of the amino acids that were produced. Results from all three methods were also consistent with respect to the location and sharpness of the peaks in the hydrolysis spectra produced by tuning the laser wavelength.

RP-HPLC produced the most accurate measurements of the height of these peaks. The procedure used for the RP-HPLC measurements are described in (http://www.ccc.uab.edu/research/shared/Peptide_Amino_Acid_Hexosamine.htm). Pure dipeptide and amino acid samples were used to prepare standards, and an internal standard, norleucine, was also used to aid in calibration of the RP-HPLC retention times. The areas under the RP-HPLC retention peaks for the unknown samples were measured and compared with the standards, and the ratio of amino acid residues to dipeptide residues was calculated using 1000 dipeptide residues as the reference. The results were reproducible to within 5%.

Samples of bovine serum albumin (BSA) were also irradiated by the laser, using the protocol that has been described. A ninhydrin colorimetric assay in liquid was used to analyse the resulting hydrolysis (Cocking, E. C. and E. W. Yemm, Biochemical Journal 58, xii (1954) and Ouzts, Mary P., "Laser Enhanced Hydrolysis of Selected Polypeptides", (PhD diss., University of Alabama, 2000)). This assay provided a quantitative measurement of the extent of hydrolysis for each sample, but it could not identify the hydrolysis products. A BSA spectrum illustrating the sharp spectral sensitivity of laser enhanced hydrolysis observed for this protein is shown in FIG. 6.

RELATED ABSORPTION SPECTRA The acid hydrolysis chemical reaction comprises protonation of the dipeptide molecule, followed by a complex, but well known sequence of charge transfers within the protonated molecule, and is completed by capture of an $H_2O$ molecule (Bailey, P. D., An Introduction to Peptide Chemistry, (John Wiley & Sons, New York (1990). The enhancement of this process by laser irradiation may be the result of changes in the internal motion of the dipeptide molecule occasioned by absorption of the laser radiation. Use of spectral information to identify the molecular transition that is induced by the laser must therefore utilize the spectrum of the protonated molecule. The IR transmission spectra of both aqueous and 6N HCl solutions of each of the dipeptides have been measured with a BioRad FTIR 40 spectrometer. These spectra were measured using a wedge cell with ZnSe windows and a mean thickness of ~10 $\mu$m. Segments of aqueous spectra measured for Thr-Asp and Ala-Ala are included in FIG. 7. There is a close coincidence between the 9P laser lines and the weak absorption peak near 1050 $cm^{-1}$ in each of these spectra. This same peak is present in the 6N HCl spectra. The laser 9R branch matches no corresponding absorption peak. Laser enhanced hydrolysis did not occur when we irradiated with 9R lines. Absorption by water is known to be stronger at 9R wavelengths than at 9P wavelengths. Our failure to observe laser enhanced hydrolysis at 9R wavelengths in samples that were largely composed of water gave the first indication that laser enhanced hydrolysis was not simply a thermal effect. Subsequent measurements revealed the sharp spectral structure of the enhanced hydrolysis that irradiation with the 9P branch produced and thus confirmed the non-thermal origin of the effect.

Also shown in FIG. 7 is our measured spectrum of N-methylacetamide (NMA) in aqueous solution. Since it is the smallest molecule containing a trans-peptide group, NMA has often been used to study polypeptide and protein spectral properties. It is often assumed that the force constants applicable to NMA are transferable to the larger molecules with only slight modification. A normal mode analysis of NMA has predicted a fundamental mode at 1070 cm-1, and this mode has previously been observed for NMA in aqueous solution at 1044 cm-1 (Bandekhar, Jagdeesh, Biochimica et Biophysica Acta 1120(2) 123–143 (1992)). This feature is clearly evident in the NMA spectrum shown in FIG. 7. A full normal mode analysis of NMA has led to the identification of the vibrational mode associated with the absorption peak at 1044 $cm^{-1}$ (Miyazawa, T., in Poly-a-Amino Acids, edited by G. D. Fasman, Marcel-Dekker, New York, 1967, pp. 69–103. This mode is shown schematically in FIG. 8.

As a first attempt to understand why such similar absorption features appear near 1050 $cm^{-1}$ in each of the spectra we have measured we invoke the general concept of infrared group frequencies. Partly because there are many as yet unassigned absorptions in the 900–1400 $cm^{-1}$ region, the reliability of this method for relating absorption in this region to molecular structure is not high (Kemp, W., Organic Spectroscopy, Third edition (W. H. Freeman and Company, New York (1991))). Nevertheless, we postulate as a working hypothesis that the ~1050 $cm^{-1}$ band results from the same molecular vibration in each dipeptide where we have observed laser enhanced hydrolysis. Moreover, we tentatively identify this vibration with the normal mode shown in FIG. 8, and we take this vibration to be the source of the laser/sample interaction leading to laser enhanced hydrolysis. However, the sharp spectral distinction in the degree of hydrolysis as the laser is tuned from line to line cannot be accounted for by the relatively broad structure of this vibrational band. We further speculate that these sharp hydrolysis peaks may result from corresponding fine structure in the absorption spectra that is produced by hindered rotation of the R' group about the N—C[R'] axis (or perhaps of the R group about the C—C[R] axis) in FIG. 8. We surmise that the change in molecular shape that accompanies the laser induced motion, whatever its origin eventually proves to be, increases the degree of exposure of the peptide bond to the surrounding environment. This enhanced exposure facilitates access to the bond by $H_2O$ molecules and thus increases the hydrolysis reaction rate.

Obviously, numerous modifications and variations on the present invention are possible in light of the above teachings. It is therefore to be understood that within the scope of the appended claims, the invention may be practiced otherwise than as specifically described herein.

What is claimed is:

1. A method of hydrolyzing a polypeptide comprising exposing the polypeptide to a tuneable molecular gas laser for a time sufficient to hydrolyze the polypeptide.

2. The method of claim 1, further comprising separating the hydrolyzed polypeptide from said polypeptide after said exposing or concurrently with said exposing.

3. A method of analyzing a polypeptide comprising exposing the polypeptide to a tuneable molecular gas laser for a time sufficient to hydrolyze the polypeptide;
    separating the hydrolyzed polypeptide from said polypeptide after said exposing or concurrently with said exposing; and
    analyzing said separated hydrolyzed polypeptide wherein said analyzing comprises determining the amino acid sequence of the polypeptide or determining the concentration of the polypeptide in a sample.

4. The method of claim 1, wherein said tuneable molecular gas laser is a $N_2O$ or $CO_2$ gas laser.

5. The method of claim 4, wherein said $N_2O$ laser is a continuous wave $^{14}N_2^{16}O$ gas laser.

6. The method of claim 4, wherein said $CO_2$ gas laser is selected from the group consisting of a $^{12}C^{16}O_2$ gas laser, a $^{12}C^{16}O^{18}O$ gas laser, a $^{12}C^{18}O_2$ gas laser, a $^{13}C^{16}O_2$ gas laser, a $^{13}C^{18}O_2$ gas laser, a $^{14}C^{16}O_2$ gas laser, a $^{14}C^{18}O_2$ gas, a $^{12}C^{17}O_2$ gas laser, a $^{13}C^{16}O^{18}O$ gas laser, and mixtures thereof.

7. The method of claim 6, wherein said $CO_2$ gas laser is a continuous wave or pulsed laser.

8. The method of claim 4, wherein said $CO_2$ gas laser is tuned to operate in the lines from one or more members selected from the group consisting of about 9R2 to about 9R60, about 9P2 to about 9P60, about 10R2 to about 10R60, and about 10P2 to about 10P60.

9. The method of claim 8, wherein said $CO_2$ gas laser is a $^{12}C^{16}O2$ gas laser tuned in accordance with the following parameters:

| Laser Line | Wavenumber (cm-1) | Wavelength ($\mu$m) |
| --- | --- | --- |
| 9P30 | 1037.43 | 9.639 |
| 9P28 | 1039.37 | 9.621 |
| 9P26 | 1041.28 | 9.604 |
| 9P24 | 1043.16 | 9.586 |
| 9P22 | 1045.02 | 9.569 |
| 9P20 | 1046.85 | 9.552 |
| 9P18 | 1048.66 | 9.536 |
| 9P16 | 1050.44 | 9.520 |
| 9P14 | 1052.20 | 9.504 |
| 9P12 | 1053.02 | 9.488 |
| 9P10 | 1055.63 | 9.473 |
| 9P8 | 1057.30 | 9.458 |

10. The method of claim 1, wherein said polypeptide is in a solution comprising water.

11. The method of claim 1, wherein said polypeptide is immobilized on a solid support.

12. The method of claim 11, wherein said solid support is selected from the group consisting of nylon membrane, agarose, polyacrylamide, and polyvinylidene difluoride teflon, plastic, glass, and metal.

13. The method of claim 3, wherein the hydrolyzed polypeptide is separated by one of the members selected from the group consisting of HPLC, ion exchange chromatography, liquid chromatography, gas chromatography, capillary electrophoresis, two dimensional combined chromatography-electrophoresis, 2D-gel electrophoresis, and combinations thereof.

14. The method of claim 3, wherein the hydrolyzed polypeptide is separated by mass spectroscopy.

15. The method of claim 14, wherein the hydrolyzed polypeptide is introduced into the mass spectrometer by MALDI or ESI.

16. The method of claim 1, wherein said hydrolyzed polypeptide is derivatized with one or more members selected from the group consisting of ninhydrin, OPA, Fmoc-Cl, NDA, PTC, and DABS-Cl.

17. The method of claim 3, wherein said analyzing comprises determining the amino acid sequence of the polypeptide.

18. The method of claim 3, wherein said analyzing comprises determining the concentration of the polypeptide in a sample.

19. The method of claim 3, wherein said analyzing comprises subjecting the hydrolyzed products to one or more members selected from the group consisting of mass spectroscopy, nuclear magnetic resonance, and infrared spectroscopy.

20. The method of claim 3, wherein said tuneable molecular gas laser is a $N_2O$ or $CO_2$ gas laser.

21. The method of claim 20, wherein said $N_2O$ laser is a continuous wave $^{14}N_2^{16}O$ gas laser.

22. The method of claim 20, wherein said $CO_2$ gas laser is selected from the group consisting of a $^{12}C^{16}O_2$ gas laser, a $^{12}C^{16}O^{18}O$ gas laser, a $^{12}C^{18}O_2$ gas laser, a $^{13}C^{16}O_2$ gas laser, a $^{13}C^{18}O_2$ gas laser, a $^{14}C^{16}O_2$ gas laser, a $^{14}C^{18}O_2$ gas, a $^{12}C^{17}O_2$ gas laser, a $^{13}C^{16}O^{18}O$ gas laser, and mixtures thereof.

23. The method of claim 22, wherein said $CO_2$ gas laser is a continuous wave or pulsed laser.

24. The method of claim 20, wherein said $CO_2$ gas laser is tuned to operate in the lines from one or more members selected from the group consisting of about 9R2 to about 9R60, about 9P2 to about 9P60, about 10R2 to about 10R60, and about 10P2 to about 10P60.

25. The method of claim 24, wherein said $CO_2$ gas laser is a $^{12}C^{16}O2$ gas laser tuned in accordance with the following parameters:

| Laser Line | Wavenumber (cm-1) | Wavelength ($\mu$m) |
|---|---|---|
| 9P30 | 1037.43 | 9.639 |
| 9P28 | 1039.37 | 9.621 |
| 9P26 | 1041.28 | 9.604 |
| 9P24 | 1043.16 | 9.586 |
| 9P22 | 1045.02 | 9.569 |
| 9P20 | 1046.85 | 9.552 |
| 9P18 | 1048.66 | 9.536 |
| 9P16 | 1050.44 | 9.520 |
| 9P14 | 1052.20 | 9.504 |
| 9P12 | 1053.02 | 9.488 |
| 9P10 | 1055.63 | 9.473 |
| 9P8 | 1057.30 | 9.458 |

26. The method of claim 3, wherein said polypeptide exposed to the tunable molecular gas laser is in a solution comprising water.

27. The method of claim 3, wherein said polypeptide is immobilized on a solid support.

28. The method of claim 27, wherein said solid support is selected from the group consisting of nylon membrane, agarose, polyacrylamide, and polyvinylidene difluoride teflon, plastic, glass, and metal.

29. The method of claim 3, wherein said hydrolyzed polypeptide is derivatized with one or more members selected from the group consisting of ninhydrin, OPA, Fmoc-Cl, NDA, PTC, and DABS-Cl.

* * * * *